United States Patent [19]
Germain

[11] Patent Number: 4,867,309
[45] Date of Patent: Sep. 19, 1989

[54] SAFE-DISPOSAL CONTAINER FOR USED HYPODERMIC NEEDLES AND THE LIKE

[75] Inventor: Bruno Germain, Saint-German-au-Mont-d'Or, France

[73] Assignee: Jean-Marie Schintgen, Paris, France

[21] Appl. No.: 209,989

[22] Filed: Jun. 22, 1988

[30] Foreign Application Priority Data

Jun. 22, 1987 [FR] France .................................. 87 08901

[51] Int. Cl.$^4$ .......................... B65D 83/10; B26F 3/00
[52] U.S. Cl. ..................................... 206/366; 225/93; 225/103; 83/167
[58] Field of Search ............................ 225/93, 97, 103; 604/110, 263; 206/365, 366; 83/167

[56] References Cited

U.S. PATENT DOCUMENTS

| | | | |
|---|---|---|---|
| 3,469,750 | 9/1969 | Vanderbeck | 83/167 X |
| 4,315,448 | 2/1982 | Ball | 83/167 |
| 4,786,280 | 11/1988 | Maeda | 604/110 |

*Primary Examiner*—Allen M. Ostrager
*Attorney, Agent, or Firm*—Frishauf, Holtz, Goodman & Woodward

[57] ABSTRACT

A prehensile container is provided for demounting and storing used hypodermic needles and/or surgical blades pending their ultimate disposal. The same hand that holds the container can actuate the closure blade by finger force to clear an orifice for passage of a used hypodermic needle. When the end of the syringe to which the needle is affixed abuts the mouthpiece of the orifice, the finger force can be released to hold the needle between the edge of an aperture of the shutter blade and an edge of the orifice, so that the needle can be separated by withdrawal of the syringe with one hand while holding the container with the other. Another exertion of finger force will let the used needle drop into the container and a second release will restore the closed condition of the container. Internal baffles obstruct the exit of stored needles, to prevent an unauthorized person from extracting a needle from the container by opening the access orifice.

16 Claims, 3 Drawing Sheets

SAFE-DISPOSAL CONTAINER FOR USED HYPODERMIC NEEDLES AND THE LIKE

The present invention concerns an enclosure device for the unmounting and sealed storing of used hypodermic needles and the like pending their destruction.

Recently, danger of transmission of virus infections which are transmissible by contact with blood, such as hepatitis and AIDS, has emphasized the importance of protecting health care personnel against infections from used hypodermic needles and the like. It has become common to provide disposable hypodermic needles, and the like, and also perfusion nozzles or other devices inserted in a living body to obtain samples of fluids such as blood for analysis or for administering a medicament or other products for medical treatment. Such disposable needles, etc. are discarded after a single use. Disposable hypodermic needles are furnished in great quantity, usually sterilized and packed individually. These are not to be sterilized after use, but are immediately destroyed or specially stored pending their destruction.

Manipulation for storage for a later destructive disposal of used hypodermic needles and the like must be accomplished in such a way that the medical personnel or others dealing with them do not risk contamination by an accidental scratch or other wound. Moreover, the stored used needles should no longer be accessible for surreptitious reuse by drug addicts or other consumers of forbidden and dangerous substances.

In consequence, it has been found desirable that the separation of the needle from the syringe should be made without manual contact with the needle in order to avoid every possible risk of accidental puncture or laceration and the consequent contamination of the victim of such an accident. For similar reasons it has been found likewise desirable to isolate the used needle immediately after its separation from the syringe in order to avoid all human contact, intentional or accidental, that might lead to an ultimate contamination of another person. Several types of devices have been proposed to facilitate manipulation of the needle storage after being separated from the syringe.

A first type of such devices is described in French Pat. No. 2,586,566. This device consists of a support for receiving the protective sheath for a sterile hypodermic needle. This easily grasped device is formed of a light cylindrical body provided coaxially with a receptacle with a control for blocking the protective sheath of the needle and also providing access at its end to the receptacle of a collar for protecting the hand holding the light cylindrical body. Thus, the used hypodermic needle is reintroduced into its protective sheath (placed in blocked position in the device) without risk of wounding the medical operator holding the device.

The device just described has some inconveniences, however, of which at least two appear to be serious.

A first inconveniences arises from the fact that the device requires two distinct manipulations by its user, first putting in place the sheath containing the sterile hypodermic needle followed by extraction of the needle from its sheath and, second, the reintroduction of the needle after its use into the sheath while using the protective collar for the hand holding the device in order to guide the needle without risk of contact.

Another inconvenience that is more serious comes to mind when it is perceived that the device does not eliminate the used needle and merely permits its reintroduction into the sheath, after which access remains possible and easy with all the risks of wounds and insecurity and thus of evident contamination.

Another type of device relates to apparatus designed to cut up used hypodermic needles and to collect the fragments in the lower part of the apparatus which is equipped with a removable container. Such a device is described, for example, in U.S. Pat. No. 4,255,996. That disclosure shows a device composed of two parts, an upper part and a lower part, fitting together to constitute a complete enclosure which, however, can still be taken apart without trouble.

The upper part has a circular access orifice for the used needle having a diameter greater than the stem end of the needle. The orifice is supplemented by a radially directed slit for holding the used needle vertical, in position for cutting, by abutment of the stem on the edges of the slit. This upper part of the apparatus is also equipped with a cutting mechanism having two pivoting parallel blades provided with an external manual control. The bottom part is equipped with a removable receptacle for collecting the cut fragments of used needles.

Although this device is of interest for the results that it obtains, it nevertheless also has inconveniences of which some may be considered important.

A first inconvenience arises from the need for the operator to have manual contact with the used needle which could possibly be contaminated, in order to separate it from the syringe, either before or after it has been cut up.

Another inconvenience appears as soon as the access orifice can remain open after the cutting operation and the enclosure is openable to separate the upper and lower parts of the closure. Thus the apparatus designed to cut up the used hypodermic needles is not sealed and leaves access possible to the cut up needles before their ultimate destruction which may be by fire, for example. In addition, cutting up the needles into particles does not exclude the infective nature of the pieces, since it is necessary to eliminate these infective particles by emptying them into another receptacle, so that their isolation is not perfect in that regard.

Still another type of equipment relates to those designed to permit separation of the used hypodermic needle from the syringe and then to provide its immediate isolation after that separation while avoiding all accidental human contact that could provoke contamination of health service personnel. Such a device has been described, for example, in PCT WO No. 82 00412 application and consists of a cylindrical container in which the upper part of the wall has a circular orifice of a diameter less than that of the stem end or tip of the hypodermic needle. This orifice is placed at the intersection of two slits in cross relation which provide a flexible zone in the top wall of the cylindrical container. The used needle affixed to the syringe is forcibly introduced in the orifice until the ferrule at its stem end passes through the top wall. Retraction of the syringe then liberates the needle, which falls to the bottom of the container.

Two major inconveniences appear. First, the permanent opening at the top leaves the container unsealed, which thereafter leaves access possible to the used needles, in addition to the risk that these needles might escape by that orifice during handling of the container.

In the second place there is the risk of deformation of the slits as the device is used to the extent that the syringe would no longer be withdrawn in a manner liberating the needle. Furthermore, the device only permits pulling off needles held by friction in the syringes and in no case needles of the vacutainer type in which the channeled stem is screwed onto the body of the syringe, making unscrewing of the needle from the syringe necessary. This apparatus is therefore quite incomplete.

The observation may also be made that there is no guiding of the needle and that it is necessary to "aim" to introduce the needle into the slits, an operation that might carry with it a risk of the needle slipping away during its introduction into the device.

Another device of the last-mentioned type is described in European Patent EP No. 0,123,247. This device consists of a receptacle in the shape of a flask for collecting loose hypodermic needles. It has a very special triangular opening for permitting engagement of the needle affixed to the syringe, followed by separation from the syringe by withdrawal and the fall of the needle into the receptacle. As soon as the needle is separated and stored in the collecting receptacle, the triangular orifice is closed by a rotary movement of its cap which prevents access to the interior of the receptacle. Although this device evidently avoids manual contact with the needle during its separation, it appears to have major inconveniences that limit its use. A first inconvenience is that the device is not easily usable when it is not in fixed position, because the opening of the triangular access orifice is produced by rotation of the cap, which involves equally the rotation of the device if it is not solidly held in position. In consequence, medical personnel have two alternatives for dealing with the device. The person may, first, move away from the patient to the storage device which is fixed in position, holding in one hand the syringe with mounted needle that may be used or infected risking any possible accident or wound for the holder or some nearby third person, the other hand seizing the cap of the device and twisting it until the triangular access orifice is open. The other alternative is that the user puts the syringe with its used needle aside, on a table perhaps, seizes the storage device with both hands, one of them rotating the cap and the other one holding the body of the device.

Another inconvenience arises from the fact that the access orifice of triangular shape does not adapt itself to the diameter of the stem of the needle which is to be separated from the syringe. In consequence, in order that the needle should be retained by the orifice, the user, after introducing the needle fixed on the syringe into the widest zone of the triangular orifice, displaces the syringe in horizontal translation until the needle is blocked by the narrowing of the triangular orifice. It results that it is difficult to avoid an occasional blockage of a needle in the triangular orifice requiring its manual disengagement with risks of wound and contamination.

A third inconvenience is the bulk of the device which makes it relatively encumbering and not easy to move because it really needs to be fixed in position either on a rolling table or in some regular position in a room for treatment or examination of patients. It should further be noted regarding this type of apparatus that it is not suitable for all types of needles and in particular for the vacutainer or epicranial types and others that are mounted by screwing on to the syringe and are therefore separable from the body of the syringe only by unscrewing.

A real need remains for an improved device that would be sealed, practical, of reasonably small dimensions for ready transportability, manually operable without risk, pocketable and handy. In particular, a device is needed in which the used needle can be easily introduced without risk and separated from the syringe without direct human contact, after which the collected needle is definitively isolated.

SUMMARY OF THE INVENTION.

It is an object of the present invention to provide an enclosure for collecting used intrusive parts of surgical device which are separable from the remainder of the surgical device for storing immediately after use without contact with the person handling the device in a manner that is secure against unauthorized access and sealed to prevent accidental escape or holding such used parts until the device itself and the parts contained in it can be permanently disposed of.

Briefly, a portable and disposable "prehensile" container is provided with a one-piece container shell having an access orifice at one end which is equipped with a plane movable closure shutter closing the orifice and capable of being displaced to a position leaving the orifice open by an externally actuatable mechanism operable by the force of a finger of a hand by which the container is held. Means are provided to urge the shutter towards the closed position for engaging at least frictionally a needle protruding through the orifice in order to facilitate demounting of the needle. The prehensile container may be shaped in various ways for efficient actuation. The "finger" that propels the actuator could, for example, be the thumb, although preferably it would be the index finger.

In an embodiment capable of serving for various kinds of disposable intrusive parts of surgical equipment, various orifice pieces may be supplied for snapping the desired one permanently in place before the device is used.

The unitary shell can be conveniently made by half shells permanently fastened together by ultrasonic welding for example, and so assembled will generally have two openings, one for inserting a pushbutton for controlling the closure and the other for seating an introduction member (mouthpiece) permitting the introduction of various kinds of needles, or the like that are to be disposed of or, if desired, just one type of disposable article such as a hypodermic needle. The shutter is mounted so that it can close or open the introduction orifice under control of a pushbutton and the latter operates against spring pressure so that the orifice is normally closed. The interior may be provided with oblique flaps opposing movement of needles towards the orifice.

The disposal container of the invention, in contrast to storage devices heretofore used for similar purposes is of dimensions small enough so that it easily fits in the pocket of a jacket, shirt,. blouse or lab coat, is easily grasped by a single free hand of the user and held in stable position while the other hand holds the surgical device on which is mounted the disposable intrusive part that has been used and is to be disposed of. The one-piece shell is elongated to fit the usual shape of intrusive pieces of surgical instruments and its cross section may be round or polygonal. The shell of course must be one piece in the sense that all the means necessary for operating it will be held within it and once it is made there will be no occasion for taking the shell apart. It can conveniently be made of two molded half shells so that before putting them together all the other parts can be introduced and put in place. Welding the two shells together in a last step of manufacture essentially closes up the device, since the insertion orifice is normally closed by the spring provided in its control mechanism.

Preferably the access orifice is provided with a frusto-conical or dished guide piece which may conveniently be shaped so that when a hypodermic needle is introduced therein the syringe, to which it is attached, can abut against it. As already mentioned, indentations may be provided at the edge of the orifice for rotary engagement with certain kinds of needle stems. These may also provide some accomodation to frictional engagement with the needle when the guide piece has the appropriate resilience and stiffness.

On the inside of the enclosure and beneath the access orifice a flat blade or plate is placed which is movable, whether in translation or rotation, and mounted so that when the device is at rest it closes the orifice. In general this closure member will be a single rigid blade having a cavity or aperture of appropriate geometric shape, preferably circular, rectangular, square, elliptical, semicircular, semielliptical, or the like. Its smallest dimension should be no smaller than the diameter of the access orifice. Most preferably, a circular aperture is provided having a diameter at least equal to that of the access orifice and mounted so that when the shutter is moved to open the access orifice this aperture will be placed coaxially with the access orifice. A stop may be provided to indicate that position to the user.

The aperture of the shutter blade, like the access orifice, can be provided with indentations on all or part of its periphery to facilitate the separation of a syringe from a screw-in type needle, by blocking the rotation of the needle, the separation being all the easier if both the orifice and the aperture in the shutter are equipped with indentations, crenelations or the like.

In a modified form, the shutter may utilize several intersecting overlapping blades in the form of an iris closure.

The shutter is connected to a control member for its movement such that a finger of the hand holding the device of the invention can produce the movement of the shutter. When it is moved, the shutter liberates the access orifice permitting the introduction of, for example, a used hypodermic needle, into the enclosure. The actuating mechanism for the shutter is equipped with return means, such as a spring, so that it will block the access orifice when it is free of finger pressure, thus making the closure of the container after its use automatic and secure.

The result is a truly "prehensile" container for avoiding personal contact with used needles or blades.

The materials used for the making of the device of the invention are, in general, thermoplastic polymeric materials such as polyolefins, polyamides, polyesters and halogenated polymers. Polymeric materials that are particularly useful, especially for a pushbutton or guide piece of an orifice, are a styrene acrylontrile known as SAN and also "½ shock" polystyrene-butadiene.

These polymeric materials may be made to include fillers such as mineral powders, such as calcium carbonate, calcium sulfate, kaolins, titanium dioxide, talc, alumina and the like, and likewise fibrous fillers may be used, either mineral or organic, as for example glass fibers, ceramic fibers and carbon fibers.

The polymeric materials can likewise receive various additives such, for example, as coloring agents, dioxide agents, antiphoton agents or the like.

In contrast to previous safety enclosures, the shape and dimensions of the prehensle container of the invention allow the medical operator to handle and manipulate it easily with one hand while the other holds the syringe on which a used needle is mounted. Its automatic return to the position closing the access orifice after the introduction of the item to be disposed of makes it unnecessary to have another manipulative step to seal the device or close it up manually.

BRIEF DESCRIPTION OF THE DRAWINGS

The invention is further described by way of illustrative example with reference to the annexed drawings, in which.

DESCRIPTION OF THE ILLUSTRATED EMBODIMENTS

Figure 1:
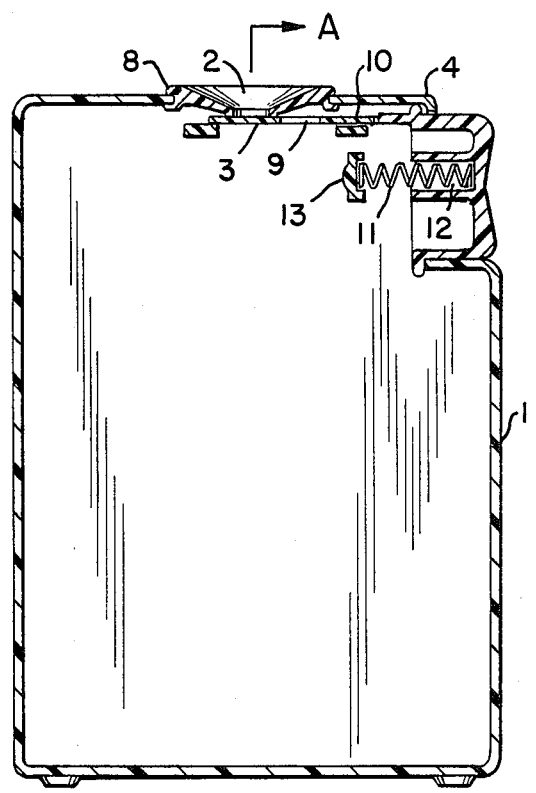
FIG. 1 is a longitudinal elevation section of a prehensile container according to the invention.
Figure 2:
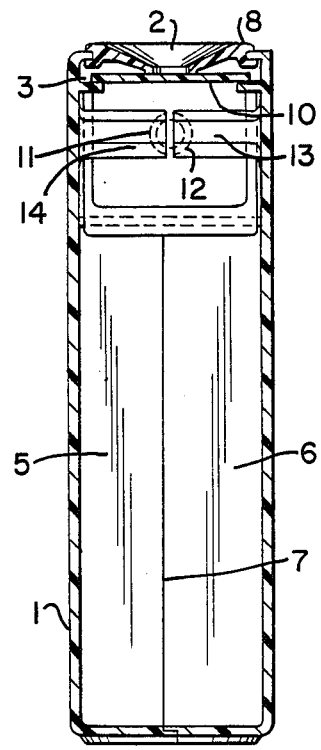
FIG. 2 is a transverse section along the line A—A of the device of FIG. 1.

As shown in FIGS. 1 and 2, the prehensile container for the unmounting and storage of used hypodermic needles or the like for disposal, is composed chiefly of a container shell 1 having an access orifice 2. Beneath the access orifice 2 and just inside the enclosure 1, a movable flat plate 3 is located under control of an actuator 4.

The container shell 1 is made of molded half shells 5 and 6 which are put together along the line 7 by welding in the final step of the assembly procedure.

The access orifice 2 is equipped with an externally and shallowly frusto-conical piece 8 serving both as a guide for a used needle and as an abutment for the syringe in which it has been used.

The shutter blade 3 has a circular aperture 9 of the same diameter as that of the orifice 2. A connection or fastening 10 holds the shutter blade 3 to a push member extension 4a of the pushbutton 4.

The actuating means for the shutter blade 3 constituted by the pushbutton 4, its extension 4a and the connection means 10 is equipped with return means 11 constituted in the illustrated case by a compression spring having one of its extremities placed in a seat 12 in the pushbutton while the other extremity abuts against the stops 13 and 14 of the respective half shells 5 and 6.

Figure 3:
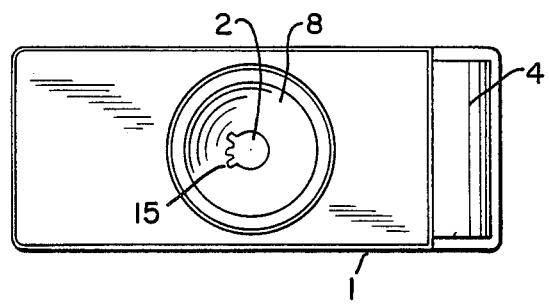
FIG. 3 is a top view of the device showing the orifice and some indentations thereof.

As shown in FIG. 3, the access orifice 2 of the shell 1 is provided with a mouthpiece 8 serving as a guide for the used needle and an abutment for the syringe. The internal periphery of the access orifice 2 has some indentations 15 that promote the blocking in position of the used needle in order to facilitate its separation from the syringe. These are particularly useful for needles affixed on the body of the syringe by screw thread, such as vacutainer and epicranial needles, for instance. The indented or crenelated portion 15 has a grasping feature for all types of needles mounted on a syringe, either by friction or by screw-threading, and facilitates separation of the needles from the syringe bodies without any risk of contact with the fingers of the health care personnel.

In practice, the above-described embodiment of the invention is used as follows:

The medical operator holding in one hand the syringe on which the used hypodermic needle is mounted grasps the enclosure device of the invention with his other hand and with one finger of that hand presses on the button 4. That movement is then transmitted by the connection 10 to the shutter blade 3. The circular aperture 9 is thereby placed in registry with the access orifice 2.

The used hypodermic needle is then introduced into the access orifice 2 and penetrates the circular aperture 9 of the shutter blade 3. The syringe carrying the used needle comes into contact with the frusto-conical mouthpiece 8.

The medical operator then releases the pressure on the pushbutton 4.

The circular aperture 9, under the action of the spring 11, tends to return to its initial position and as a result engages and holds the stem of the needle and blocks its withdrawal. Whether the stem is held by friction or is a grooved stem held by the indentations, it is readily separated from the syringe either by friction or by imposing a half turn on the syringe to produce an unscrewing of the used needle to disengage it from the body of the syringe if it is a twist-locked type of needle. In each case the used needle is then easily separated by means of a simple withdrawal of the syringe. The used hypodermic needle then falls into the interior of the enclosure 1.

The shutter blade 3, now released, returns to its initial position under the action of the spring 11 and thus closes the access orifice 2, hermetically isolating the used needles in the container without risk that these needles might come out of the container and assuring a real security.

Figure 4:
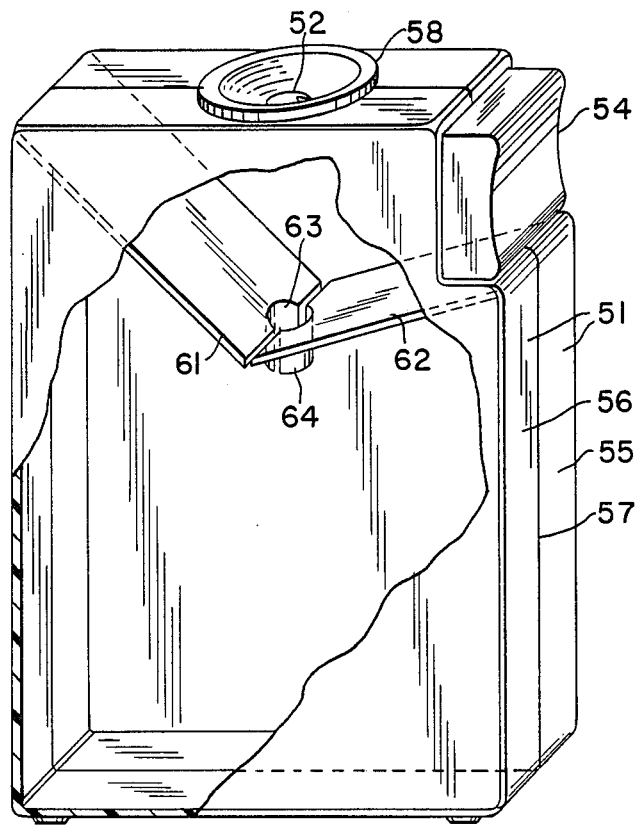
FIG. 4 is a scheatized isometric view of anti-return baffles located in like that of FIG. 1.
Figure 5:
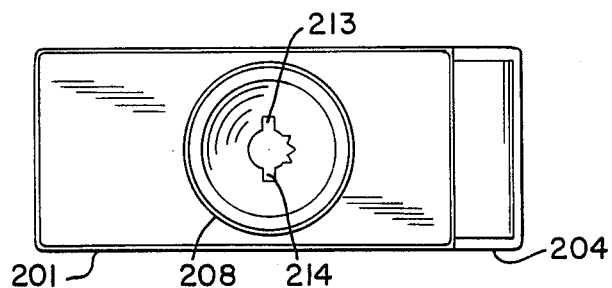
FIG. 5 is a top view of a prehensile container according to the invention having a modified shape of orifice.

FIG. 4 shows the provision of oblique flaps 61 and 62 in a container of the kind shown in FIGS. 3, 4, and 5 for opposing movement of the needles towards the orifice 52 of the container. Of course in the rest position the orifice 52 is closed by the shutter blade, but there is still a slight risk that some unauthorized person, perhaps driven beyond reason by drug addiction, might surreptitiously get hold of the box as a source of needles that have only been used once and try to get a needle out by pushing the orifice control piece 54. Of course the container shell 51 must be long enough (tall enough) for the needles to fall through the slot between the baffles 61 and 62. As shown in FIG. 4 in the middle of that slot the baffles have cutouts with downward extending portions 63 and 64 to guide the needle into the lower portion of the interior of the shell 51. The parts 63 and 64 may be regarded as parts of a tubular collar.

FIG. 4 is quite schematically drawn, leaving out the shutter for the orifice and other details, but the shell 51 corresponds to the shell 1 of FIG. 1, the pusher-actuator 54 to the pushbutton 4 of FIG. 1 and the dished mouthpiece 58 for the orifice 52 to the dished mouthpiece 8 for the orifice 2 of FIG. 1.

The baffles 61 and 62 can conveniently be of the same material as the shell 1. It is convenient to affix them on only one of the originally separate half shells 55 and 56 which are ultimately welded together along the seam 57. Both baffles can be attached to the same half shell, or one of them to each half shell, in each case being fastened along one oblique baffle edge joining a wide side wall of the container and also along a short length running toward the seam 57. The baffles 61 and 62 can be injection-molded with the half shell or half shells to which they are attached or features can be injection-molded into the half shells such that the baffles can be slipped into place just before the two half shells are put together to form a unitary shell 51.

FIG. 5 is a top view of a modified from of prehensile container according to the invention in which the orifice 202 is shaped to admit needles of the so-called "butterfly" type as well as other type of hypodermic needles. The mouthpiece 208, the shell 201 and the pushbutton 204 are shown, but other details of the device are omitted since they correspond to what is disclosed in FIGS. 1–4. The shutter blade (not shown in FIG. 5) of course needs to be wider and is preferably equipped with an aperture which has the same shape as the orifice 202. The notches are wide enough for easy insertion of a butterfly type of needle. The shutter blade will narrow them when the pressure on the button 204 is released. The notches 213 and 214 do not interfere with the acceptance and subsequent blocking in place of various kinds of round needles, whether they need to be unscrewed or not. not.

Figure 6:
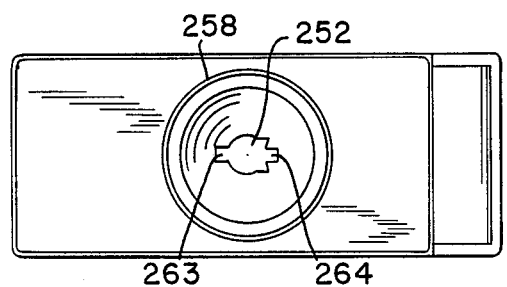
FIG. 6 is a top view of a prehensile container according to the invention having another modified orifice shape.

FIG. 5 FIG. 5 is preferred over FIG. 6, but FIG. 6 is shown as another possibility for the same purpose. Corresponding parts of FIG. 6 are provided with reference numerals higher by 50 than those of FIG. 5.

Figure 7:
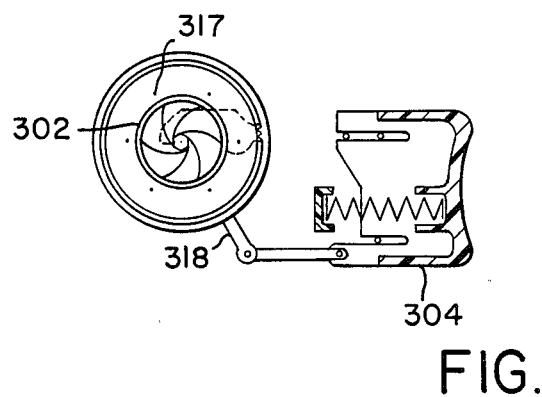
FIG. 7 is an illustration (bottom view) of an iris closure mechanism for the container orifice.

FIG. 7 shows the use of an iris diaphram for the shutter. FIG. 7 is a view from the inside of the prehensile container, the pushbutton 304 being shown partly in section. The iris diaphragm mechanism 317 is mounted in the same way as in a camera lens assembly. The lever 318 is connected to swing the control ring (not shown) which moves the blades to open the diaphragm as the pushbutton is pushed in. In the rest position of the pushbutton 304 the iris diaphragm is fully or substantially closed, whereas with the pushbutton fully depressed, the blades clear the aperture 302.

Although the invention has been described with reference to particular illustrative embodiments, it will be understood that modifications and variations are possible within the inventive concept.

What is claimed:
1. Portable and disposable prehensile container for demounting and storing used hypodermic needles and the like for their ultimate disposal, comprising:
   a unitary container shell having an orifice for access of hypodermic needles to its interior;
   a flat plate closure member for said orifice which member is mounted in the interior of said container shell beneath said orifice for movement permitting said closure member to be displaced between a first position in which it closes said orifice and a second position in which it leaves said orifice open to the interior of said container shell;
   means for displacing said closure member from said first position to said second position by force exerted by a finger of a human hand by which said portable container is firmly held,
   and means responsive to release of said human hand finger force for displacing said closure member away from said second position and towards said first position and thereby engaging, at least fric- tionally, a needle protruding through said orifice and thereby facilitating the demounting of said needle from a device on which it was mounted.

2. Prehensile container according to claim 1, wherein the periphery of said orifice is at least in part provided with indentations or crenelations.

3. Prehensile container according to claim 2, wherein said orifice is externally equipped with a frusto-conical mouthpiece for guiding a used hypodermic needle and for abutment of a syringe on which said needle is mounted.

4. Prehensile container according to claim 1, wherein said flat plate closure member is a single rigid blade.

5. Prehensile container according to claim 4, wherein said blade has an aperture of which the smallest dimension is at least equal to the diameter of said orifice.

6. Prehensile container according to claim 4, wherein said blade has an aperture of a shape selected from the group consisting of square, rectangular, circular, semrcircular, elliptical and semielliptical shapes.

7. Prehensile container according to claim 6, wherein the periphery of said aperture is at least in part provided with indentations or crenelations.

8. Prehensile container according to claim 1, wherein said means for displacing said closure member comprises a pushbutton equipped with means for connecting said pushbutton to said closure member, said means for displacing said closure member away from said second position and towards said first position serving also for return of said pushbutton to its rest position and said closure member to said first position.

9. Prehensile container according to claim 8, wherein said means for displacing said closure member towards said first position is a spring.

10. Prehensile container according to claim 1, wherein said container shell is equipped in its interior with baffle means opposing the return of a stored needle through said orifice of said container shell.

11. Prehensile container according to claim 1, wherein said baffle means is formed by at least one plate affixed at some of its edges to said container shell.

12. Prehensile container according to claim 11, wherein said baffle means is provided with an aperture for passage of a needle on its way into the interior of said container shell from said orifice of said container shell.

13. Prehensile container according to claim 12, wherein said aperture of said baffle means is provided with at least a partial tubular collar.

14. Portable and disposable prehensile container for demounting and storing detachable intrusive disposable parts of surgical and medical instruments in a manner avoiding contact with the person of attendant personnel, pending the ultimate disposal of the container and the parts stored therein, comprising:

a unitary container shell having an orifice for access of a said disposable intrusive part of a surgical or medical instrument for storage thereof in the interior of the container;

a flat plate closure device for said orifice which device is mounted in the interior of said container shell beneath said orifice and has an actuating control which is displaceable between a first position in which it closes said orifice and a second position in which it leaves said orifice open to the interior of said container shell;

means for displacing said actuating control from said first position to said second position by force exerted by a finger of a human hand by which said portable container is firmly held, and means responsive to release of said human hand finger for displacing said actuating control away from said second position and towards said first position for engaging, at least frictionally, said disposable intrusive instrument part protruding through said orifice and thereby facilitating the demounting of said part from an instrument on which it was mounted.

15. Prehensile container according to claim 14, wherein said container shell is equipped in its interior with baffle means opposing the return from said orifice of a stored used part.

16. Portable and disposable prehensile container for demounting and storing used hypodermic needles and the like for their ultimate disposal, comprising:

a unitary container shell having an orifice for access of hypodermic needles to its interior;

a closure device having a plurality of flat blades crossing over each other, pivoted and commonly driven in the pattern of an iris diaphragm closure mounted in the interior of said container shell beneath said orifice and having an actuatable control movable between a first position in which said orifice is closed and a second position in which said orifice is left open to the interior of said container shell means for displacing said actuation control of said closure from said first position to said second position by force exerted by a finger of a human hand by which said portable container is firmly held, and means responsive to the release of said human hand finger force for displacing said actuation means away from said second position and towards said first position and thereby engaging, at least frictionally, a needle protruding through said orifice and thereby facilitating the demounting of said needle from a device on which it was mounted.

* * * * *